United States Patent
Bamba

(10) Patent No.: US 7,361,362 B2
(45) Date of Patent: Apr. 22, 2008

(54) EMULSION COMPOSITION

(75) Inventor: Takaaki Bamba, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 402 days.

(21) Appl. No.: 10/467,858

(22) PCT Filed: Mar. 13, 2001

(86) PCT No.: PCT/JP01/01959

§ 371 (c)(1),
(2), (4) Date: Aug. 13, 2003

(87) PCT Pub. No.: WO02/072054

PCT Pub. Date: Sep. 19, 2002

(65) Prior Publication Data

US 2004/0067211 A1    Apr. 8, 2004

(51) Int. Cl.
*A61K 9/107*    (2006.01)
*A61K 47/34*    (2006.01)
*A61K 31/17*    (2006.01)

(52) U.S. Cl. .................. 424/401; 514/975; 514/847

(58) Field of Classification Search ............. 424/401; 514/975, 847
See application file for complete search history.

(56) References Cited

U.S. PATENT DOCUMENTS

| | | | |
|---|---|---|---|
| 3,562,786 A | 2/1971 | Bailey et al. | |
| 5,853,711 A * | 12/1998 | Nakamura et al. | 424/78.03 |
| 5,916,548 A | 6/1999 | Hutchins et al. | |
| 6,607,718 B1 * | 8/2003 | Okuno et al. | 424/70.13 |

OTHER PUBLICATIONS

Patent Abstracts of Japan, No. 2000-256126, Sep. 19, 2000 & abstract.
Patent Abstracts of Japan, No. 11-255640, Sep. 21, 1999 & abstract.
Patent Abstracts of Japan, No. 07-285835, Oct. 31, 1995 & abstract.

* cited by examiner

*Primary Examiner*—Edward Webman
(74) *Attorney, Agent, or Firm*—Townsend & Banta

(57) ABSTRACT

The present invention is an emulsified composition comprising (a) 0.01-5 wt % polysiloxane-polyoxyalkylene copolymer, (b) 0.05-1 wt % nonionic surfactant, (c) 10-30 wt % humectant, and (d) 1-50 wt % urea. The present invention provides an emulsified formulation of a urea-containing emulsified composition that has a superior emulsifying ability even with a lowered blend ratio of the surfactant, suppresses tingling due to urea, and is good feeling of use without stickiness even with a high blend ratio of the humectant.

15 Claims, No Drawings

EMULSION COMPOSITION

The present application is a national stage PCT application claiming the benefit of international application serial No. PCT/JP01/01959, filed Mar. 13, 2001.

TECHICAL FIELD

The present invention relates to an emulsified composition containing urea.

More particularly, the present invention relates to an emulsified composition containing urea that has a superior moisture retaining effect while reducing the stimulation from urea and gives a very refreshing feeling at the time of application.

BACKGROUND ART

In skin care cosmetics and endermic liniments, natural moisturizing factors (NMF) and humectants are used to maintain beautiful skin conditions and to prevent and/or alleviate rough skin.

Among natural moisturing factors, urea is well known to have a corneum softening effect and a skin roughness preventing effect. However, in a system with blended-in urea, there is a problem in that skin irritation such as tingling occurs occasionally.

In such a case there is a way to control tingling due to urea by adding a large amount of a humectant. However, the addition of a large amount of a humectant causes significant stickiness when the cosmetic is applied on the skin because of a high viscosity and hygroscopicity of the humectant itself, resulting in reduced usability.

On the other hand, in emulsified cosmetics, a surfactant is used as an emulsifying agent; however, for the sake of safety of consumers with sensitive skin, the lowest possible blend ratio is desirable.

In the aforementioned current situation, an urea-containing composition in the form of an emulsified formulation is desired that retains a superior emulsifying ability even with a lowered blend ratio of the surfactant and is easy to use without stickiness even with a high blend ratio of the humectant.

The present invention was carried out in view of the aforementioned situation, and its object is to provide an emulsified formulation of a urea-containing emulsified composition that has a superior emulsifying ability even with a lowered blend ratio of the surfactant, suppresses tingling due to the urea, and having good feeling of use without stickiness even with a high blend ratio of the humectant.

DISCLOSURE OF INVENTION

The present invention provides an emulsified composition comprising (a) 0.01-5 wt % polysiloxane-polyoxyalkylene copolymer, (b) 0.05-1 wt % non-ionic surfactant, (c) 10-30 wt % humectant, and (d) 1-50 wt % urea.

Also, the present invention provides said emulsified composition wherein said (a) ingredient is a compolymer represented by the following chemical formula (I):

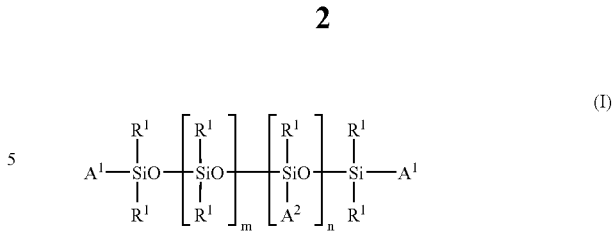

The symbols in formula (I) are described below:

$R^1$: An alkyl group having 1-6 carbon atoms, or phenyl group independently $A^1$, $A^2$: An alkyl group having 1-6 carbon atoms, or phenyl group or a polyoxyalkylene group represented by the following chemical formula (II), independently:

{In chemical formula (II), $R^2$ denotes a hydrogen atom, acyl group, or an alkyl group having 1-6 carbon atoms, a denotes an integer 0-50, and b denotes an integer 0-50. a and b cannot be 0 at the same time.}, wherein at least one of $A^1$ and $A^2$ denotes a polyoxyalkylene group represented by the following chemical formula (II):

m: An integer 50-1000;
n: An integer 1-50.

Furthermore, the present invention provides said emulsified composition wherein said emulsified composition is an endermic liniment.

Also, the present invention provides said emulsified composition wherein said emulsified composition is an emulsified cosmetic.

The present invention provides an emulsified formulation of a urea-containing emulsified composition that has a superior emulsifying ability even with a lowered blend ratio of the surfactant, suppresses tingling due to urea, and having good feeling of use without stickiness even with a high blend ratio of the humectant.

The present invention is used preferably for an endermic liniment, and for an emulsified cosmectic in particular.

BEST MODE FOR CARRYING OUT THE INVENTION

The present invention is described in detail below.

For the polysiloxane-polyoxyalkylene copolymer which is ingredient (a) contained in the emulsified composition of the present invention, a copolymer represented by the following chemical formula (I) is preferably used:

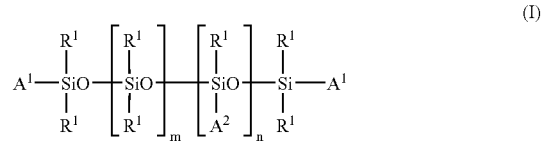

In chemical formula (I), $R^1$: An alkyl group having 1-6 carbon atoms or phenyl group independently $A^1$, $A^2$: An alkyl group having 1-6 carbon atoms, or phenyl group or a polyoxyalkylene group represented by the following chemical formula (II), independently:

{In chemical formula (II), $R^2$ denotes a hydrogen atom, acyl group, or an alkyl group having 1-6 carbon atoms, a denotes an integer 0-50, and b denotes an integer 0-50. a and b cannot be 0 at the same time.}, wherein at least one of $A^1$ and $A^2$ denotes a polyoxyalkylene group represented by the following chemical formula (II):

m: An integer 50-1000;

n: An integer 1-50.

Of the above, chemical formula (II) is preferable for $A^2$. For each of $R^1$, a methyl group is preferable.

Ingredient (a) can be prepared by making a polyoxyalkylene compound having a double bond group at its end react with a siloxane compound having a hydrosilyl group end which reacts with the reactive end group of the polyoxyalkylene group; however, the preparation method is not limited to this method. Ingredient (a) is commercially available as, for example, "Silicone SC9450N" (from Shin-Etsu Chemical Co., Ltd.).

The blend ratio of ingredient (a) is 0.01-5 wt %, preferably 0.1-1 wt %, of the composition of the present invention.

The non-ionic surfactant used for ingredient (b) is one of those which is commonly blended in cosmetics; hydrophilic non-ionic surfactants are preferably used. These surfactants for the present invention are preferably those with a HLB of 9 or higher.

Examples of the the hydrophilic nonionic surfactant include POE sorbitan fatty acid esters such as POE sorbitan monooleate, POE sorbitan monostearate, POE sorbitan monolaurate, and POE sorbitan tetraoleate, POE sorbitol fatty acid esters such as POE sorbitol monolaurate, POE sorbitol monooleate, POE sorbitolpentaoleate, and POE sorbitol monostearate, POE glycerin fatty acid esters such as POE glycerin monostearate and POE glycerin triisostearate, POE fatty acid esters such as POE monooleate, POE alkylethers such as POE lauryl ether, POE alkyl phenyl ethers such as POE octylphenyl ether, POE/POP alkylethers such as POE/POP cetyl ether, tetra POE/tetra POE ethylene diamine condensates, POE castor oil or hydrogenated castor oil derivatives, POE beeswax/lanolin derivatives, alkanol amides such as monoethanol amide laurate, POE propylene glycol fatty acid esters, POE alkylamines, POE aliphatic acid amides, sucrose fatty acid esters, POE nonylphenylformaldehyde condensates, alkyl ethoxy dimethylamine oxide, trioleylphosphoric acid, and polyglycerin fatty acid esters.

The blend ratio of ingredient (b) is 0.05-1 wt %, preferably 0.1-0.5 wt %, of the composition of the present invention. In the present invention, a superior emulsification effect can be obtained even with such a low blend ratio of ingredient (b).

The humectant used for ingredient (c) includes everything that can typically be blended in cosmetics as a humectant.

Specific examples include polyethylene glycol, glycerin, 1,3-butylene glycol, erythritol, sorbitol, xylitol, maltitol, mucopolysaccharide, hyaluronic acid, chondroitin sulfate and chitosan; but the humectant is not limited to these examples. One, two or more humectants can be selected for use.

The blend ratio of ingredient (c) is 10-30 wt %, preferably 10-15 wt %, of the composition of the present invention. The present invention does not cause stickiness and retains a superior feeling at the time of application (refreshing feeling) even with such a high blend ratio of ingredient (c).

The urea used for ingredient (d) is represented by the chemical formula $H_2CONH_2$; any urea used in the fields of cosmetics or medical drugs can be used.

The blend ratio of ingredient (d) is 1-50 wt %, preferably 3-20 wt %, of the composition of the present invention. In the present invention, there is no tingling feeling, the irritation is low, and usability (moist feeling) is superior even with such a relatively high blend ratio of ingredient (d).

With the present invention, by means of blending a polysiloxane-polyoxyalkylene copolymer in a urea-containing formulation, a substantial reduction in the blend ratio of surfactant was made possible, allowing preparation of an emulsified composition with superior usability which does not become sticky even with a higher blend ratio of the humectant.

That is, the present invention is a technique to prepare an emulsified formulation with good feeling of use and without stickiness by blending in a polysiloxane-polyoxyalkylene copolymer and using a small amount of a nonionic surfactant for emulsification to reduce irritation due to urea.

The emulsified composition of the present invention is preferably used as an emulsified formulation of an endermic liniment, and is particularly preferable for use in cosmetics in which feeling of use is deemed important. It is used for many types of cosmetics including basic cosmetics such as lotions, emulsions, creams, and packs, makeup cosmetics such as lipsticks and foundations, hair care products such as shampoos, rinses, and hair dyes, as well as special cosmetics such as sunscreen.

In addition to the aforementioned essential ingredients, other ingredients used in endermic liniments such as cosmetics and medical drugs can be blended in the emulsified composition of the present invention as necessary; examples of such ingredients include oils, humectants, antioxidants, other surfactants, preservatives, amino acids, perfumes, alcohols, coloring agents, powders, and drugs.

Specific examples include hydrocarbons such as liquid petrolatum, squalane, and petrolatum; fats and oils such as avocado oil, tsubaki oil, macademia nut oil, olive oil, and lanolin; waxes such as jojoba oil, carnauba wax, and candelilla wax, silicones such as dimethyl polysiloxane and methylphenylsiloxane; higher alcohols such as capryl alcohol, lauryl alcohol, myristyl alcohol, cetyl alcohol, cholesterol, and phytosterol; higher fatty acids such as caprylic acid, myristic acid, palmitic acid, stearic acid, behenic acid, lanolin aliphatic acid, linolic acid, linolenic acid; lower alcohols such as ethanol; antioxidants such as butylated hydroxy toluene, tocopherol, and phytin; antimicrobial agents such as benzoic acid, salicylic acid, sorbic acid, para oxybenzoic acid alkyl ester, and hexachlorophene.

Also, ultraviolet light absorbents can be blended in; examples include the paraminobenzoic acid-type ultraviolet light absorbent, anthranilic acid-type ultraviolet light absorbent, salicylic acid-type ultraviolet light absorbent, cinnamic acid-type ultraviolet light absorbent, benzophenone-type ultraviolet light absorbent, sugar-type ultraviolet light absorbent, 3-(4'-methylbenzylidene)-d-camphor, 3-benzylidene-d, 1-camphor, urocanic acid, urocanic acid ethyl ester, 2-phenyl-5-methyl benzoxazol, 2,2'-hydroxy-5-methylphenyl benzotriazol, 2-(2'-hydroxy-5'-t-octylphenyl) benzotriazol, 2-(2'-hydroxy-5'-methylphenyl benzotriazol, dibenzaladine, dianisoylmethane, 4-methoxy-4'-t-butyl dibenzoylmethane, and 5-(3,3-dimethyl-2-norbornylidene)-3-pentane-2-one).

The following can be blended in as well: amino acids such as glycin, alanine, valine, leucine, threonine, phenyl-alanine, tyrosine, aspartic acid, asparagine, glutamine, taurine, arginine, and histidine, as well as their alkali metal salts and chlorides; organic acids such as acylsarcosinic acid (sodium N-lauroyl sarcosinate, for example), glutathione, citric acid, malic acid, tartaric acid, and lactic acid; vitamins including vitamin A and its derivatives, vitamin B's such as vitamin $B_6$ hydrochloride, vitamin $B_6$ tripalmitate, vitamin B6 dioctanoate, vitamin B2 and its derivatives, vitamin $B_{12}$, and vitamin $B_{15}$, vitamin C's such as ascorbic acid, ascorbic acid sulfuric ester (salt), ascorbic acid phosphoric ester (salt), ascrobic acid dipalmitate, vitamin E's such as α-tocopherol, β-tocopherol, γ-tocopherol, and vitamin E acetate, vitamin D's, vitamin H, pantothenic acid, and pantethine; various drugs including icotinamide, nicotinic acid benzil, γ-oryzanol, allantoin, glycyrrhizic acid (salt), glycyrrhetimic acid and its derivative, hinokitiol, bi sabot roll, eucalyptol, thymol, inositol, saponins such as saikosaponin, carrot saponin, sponge gourd saponin, and soapberry saponin, pantothenyl ethyl ether, ethynylestradiol, tranexamic acid, arbutin, cepharanthine, and placenta extract.

Also, for example, plant extracts from Rumex japonicus, Sophora angustifolia, Nuphar japonicum, orange, sage, Achillea sibirica, Malva sylvestris, Swertia japonica, thyme, Ligusticum acutilobum, Picea jezoensis, Birch, horsetail, sponge gourd, horse chestnut tree, creeping saxifrage, arnica, lily, mugwort, Paeonia lactiflora, aloe, gardenia, Scomberomorus niphonius, and white Lily, as well as pigments, neutralizers, antioxidants, perfume, and purified water can be blended in.

EXAMPLES

The present invention is described in detail below based on Examples; however, the present invention is not limited to these Examples. The blend ratios are in wt % units.

Examples 1-2 and Comparative Examples 1-3

A cream with the composition shown the following Table 1 was obtained by means of a conventional method. Actual use testing (moist feeling, smooth feeling, and tingling feeling) was conducted using this cream. In addition, the skin conductance value was measured. The emulsification stability was evaluated as well. The results are shown in Table 1.

For the "polysiloxane-polyoxyalkylene copolymer" in Table 1, the aforementioned chemical formula (I) was used wherein $R^1$ was a methyl group, $A^1$ was a methyl group, and $A^2$ was the group represented by chemical formula 2 (approximate molecular weight 6,000).

<Actual use testing>

A panel of ten female specialists actually applied the sample on the skin and evaluated the moist feeling, smooth feeling (non-stickiness), and tingling feeling based on the following criteria.

[Moist Feeling]

(Evaluation Criteria)
○: Eight or more reported a moist feeling.
Δ: Three to seven reported a moist feeling.
X: Two or less reported a moist feeling.

[Smooth Feeling (non-stickiness)]

(Evaluation Criteria)
○: Eight or more reported a smooth feeling (non-stickiness).
Δ: Three to seven reported a smooth feeling (non-stickiness).
X: Two or less reported a smooth feeling (non-stickiness).

[Tingling Feeling]

(Evaluation Criteria)
○: Eight or more reported the absence of a tingling feeling.
Δ: Three to seven reported the absence of a tingling feeling.
X: Two or less reported the absence of a tingling feeling.

<Skin Conductance Value>

Each of the samples was applied on a specific site of the skin once a day, and, after allowing to stand for three minutes, washed off with purified water and wiped off with absorbent cotton. This procedure was repeated for two weeks and then the skin conductance of the applied site was measured.

<Emulsification Stability>

Each sample was stored at 50° C. for a month and the emulsification state was visually observed.

(Evaluation Criteria)
○: No separation was observed and the emulsification condition was good.
X: Separation was observed.

TABLE 1

| Ingredients | Example 1 | Example 2 | Comparative example 1 | Comparative example 2 | Comparative example 3 |
|---|---|---|---|---|---|
| Cetanol | 2.0 | 2.0 | 2.0 | 2.0 | 2.0 |
| Stearyl alcohol | 1.0 | 1.0 | 1.0 | 1.0 | 1.0 |
| Stearic acid | 1.0 | 1.0 | 1.0 | 1.0 | 1.0 |
| White vaseline | — | 3.0 | — | 3.0 | — |
| middle-chain fatty acid ester | 2.0 | 2.0 | 2.0 | 2.0 | 2.0 |
| Dimethyl polysiloxane | 2.0 | 2.0 | 2.0 | 2.0 | 2.0 |
| Polysiloxane-polyoxyalkylene copolymer | 0.3 | 0.5 | — | — | — |
| Paraben | 0.2 | 0.2 | 0.2 | 0.2 | 0.2 |
| "Polysorbate 80" | — | 0.3 | — | 0.3 | — |
| Polyoxyethylene hydrogenated castor oil 60 | 0.5 | — | 2.0 | — | 2.0 |
| Urea | 10.0 | 10.0 | 10.0 | 10.0 | 10.0 |
| Glycerin | 15.0 | 12.0 | 15.0 | 12.0 | — |
| Propylene glycol | 5.0 | — | 5.0 | — | 5.0 |
| 1,3-butylene glycol | — | 5.0 | — | 5.0 | — |
| Caustic soda | 0.05 | 0.05 | 0.05 | 0.05 | 0.05 |
| Purified water | Balance | Balance | Balance | Balance | Balance |
| Moist feeling | ○ | ○ | ○ | ○ | X |
| Smooth feeling | ○ | ○ | X | X | Δ |

TABLE 1-continued

| Ingredients | Example 1 | Example 2 | Comparative example 1 | Comparative example 2 | Comparative example 3 |
|---|---|---|---|---|---|
| Tingling feeling | ○ | ○ | ○ | ○ | x |
| Skin conductance value | 213 | 187 | 200 | 194 | 116 |
| Emulsification stability (Stored for one month at 50° C.) | ○ | ○ | x | x | x |

INDUSTRIAL APPLICABILITY

As described above, the present invention provides an emulsified formulation of a urea-containing emulsified composition that has a superior emulsifying ability even with a lowered blend ratio of the surfactant, suppresses tingling feeling due to urea, and is easy to use without stickiness even with a high blend ratio of the humectant.

The emulsified composition of the present invention is preferably used for endermic liniments such as cosmetics.

The invention claimed is:

1. An emulsified composition comprising
(a) 0.01-5 wt % polysiloxane-polyoxyalkylene copolymer is represented by the following chemical formula (I):

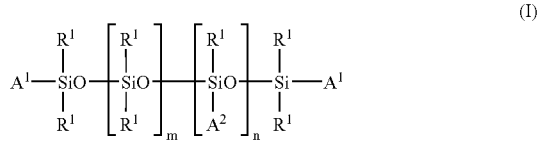

wherein $R^1$ is an alkyl group having 1-6 carbon atoms or phenyl group independently, $A^1$ and $A^2$ are an alkyl group having 1-6 carbon atoms, phenyl group or a polyoxyalkylene group represented by the following chemical formula (II), independently:

wherein in chemical formula (II), $R^2$ denotes a hydrogen atom, acyl group, or an alkyl group having 1-6 carbon atoms, a denotes an integer 0-50, and b denotes an integer 0-50, a and b cannot be 0 at the same time, wherein at least one of $A^1$ and $A^2$ denotes a polyoxyalkylene group represented by chemical formula (II), m is an integer of 50-1000; and
n is an integer of 1-50,
(b) 0.05-1 wt % nonionic surfactant selected from the group consisting of polyoxyethylene sorbitan fatty acid esters and polyoxyethylene hydrogenated castor oil,
(c) 10-30 wt % humectant, and
(d) 1-50 wt % urea.

2. The emulsified composition of claim 1, wherein said emulsified composition is an emulsified cosmetic.

3. The emulsified composition of claim 1, wherein said emulsified composition is an endermic liniment.

4. The emulsified composition of claim 1, wherein ingredient (b) is a hydrophilic non-ionic surfactant with a HLB of 9 or higher.

5. The emulsified composition of claim 1, wherein the ingredient (b) has a blend ratio of 0.1-0.5 wt % of the composition.

6. The emulsified composition of claim 1, wherein the humectant ingredient (c) has a blend ratio of 10-15 wt % of the composition.

7. The emulsified composition of claim 1, wherein the urea ingredient (d) has a blend ratio of 3-20 wt % of the composition.

8. A process of moisturizing skin comprising the step of applying to the skin the emulsified composition of claim 1.

9. A process of moisturizing skin comprising the step of applying to the skin the emulsified composition of claim 2.

10. A process of moisturizing skin comprising the step of applying to the skin the emulsified composition of claim 3.

11. A process of moisturizing skin comprising the step of applying to the skin the emulsified composition of claim 4.

12. A process of moisturizing skin comprising the step of applying to the skin the emulsified composition of claim 5.

13. A process of moisturizing skin comprising the step of applying to the skin the emulsified composition of claim 6.

14. A process of moisturizing skin comprising the step of applying to the skin the emulsified composition of claim 7.

15. The emulsified composition of claim 1, wherein in the chemical formula (I) $R^1$ is a methyl group, $A^1$ is a methyl group, and $A^2$ is a group represented by the chemical formula (II) having an approximate molecular weight of 6,000.

* * * * *